June 8, 1965 W. ZOMBORY ET AL Plant Pat. 2,531
ROSE PLANT
Filed March 19, 1964
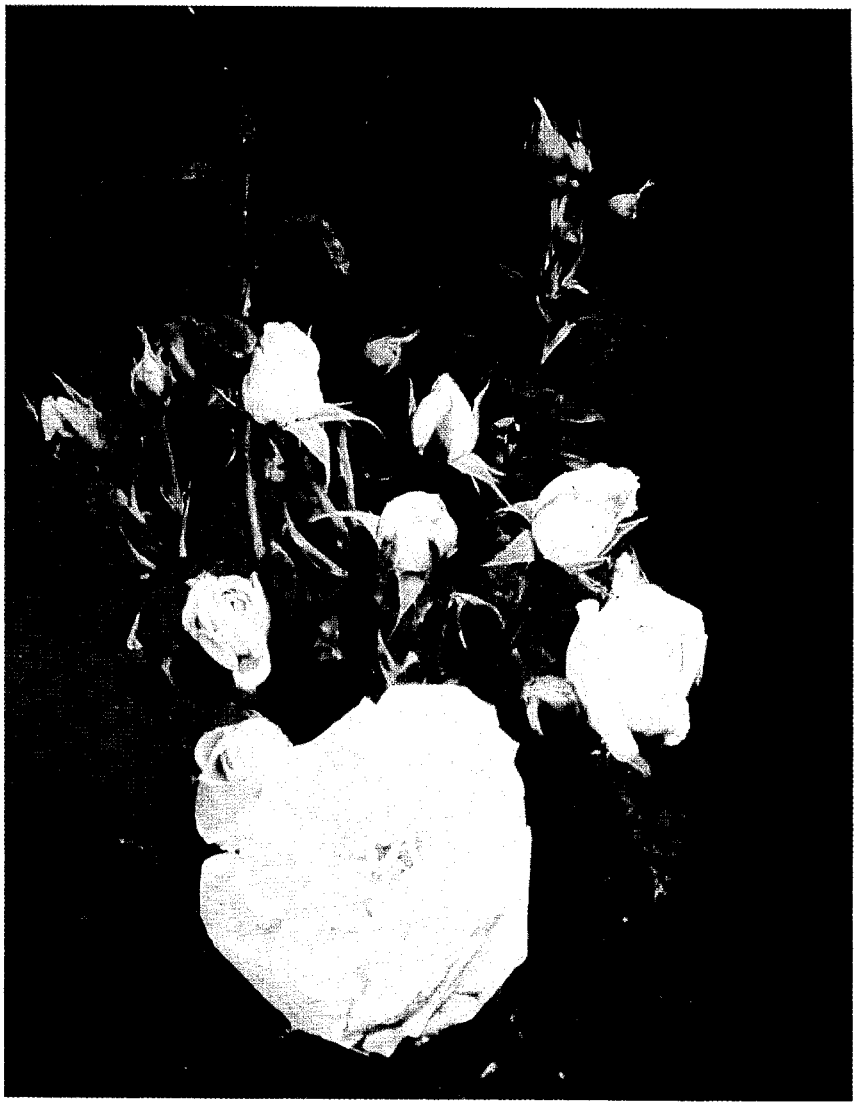
Inventors.
William Zombory and
Sophia B. Zombory
By: Robb & Robb
Attorneys.

United States Patent Office

Plant Pat. 2,531
Patented June 8, 1965

2,531
ROSE PLANT

William Zombory and Sophia B. Zombory, Detroit, Mich., assignors to Jackson & Perkins Company, Newark, N.Y., a corporation of New York Filed Mar. 19, 1964, Ser. No. 353,308
1 Claim. (Cl. Plt.—5)

The present invention relates to a new and distinct variety of rose plant of the climber class, which was originated by us by crossing an unnamed and unpatented seedling of "New Dawn" (Plant Patent No. 1)×"Geranium Red" (Plant Patent No. 811) with the variety "Fashion" (Plant Patent No. 789).

The primary objective of this breeding was to create a new and improved everblooming climbing rose variety having the general characteristics of the variety "New Dawn," but bearing flowers of a different color. This objective was fully achieved, as evidenced by the following unique combination of characteristics which are outstanding in the new variety and which distinguish it from its parents, as well as from all other varieties of which we are aware:

(1) General characteristics corresponding to those of "New Dawn," except principally the flower color;

(2) A habit of bearing the blooms on the terminal bottom breaks, with repeating blooms being borne on the side shoots of the older wood, as in the variety "New Dawn";

(3) Large double flowers of good petalage, with the flowers averaging 4 inches in diameter and having from 40 to 45 petals; and (4) A distinctive and attractive general color tonality of the flowers corresponding to Rose Red, lightly overcast with Tyrian Rose.

Asexual reproduction of our new variety by budding, as performed at Detroit, Michigan, and also at Newark, New York, shows that the aforementioned characteristics and distinctions come true to form and are established and transmitted through succeeding propagations.

The accompanying drawing shows typical specimens of the vegetative growth and flowers of our new variety in different stages of development and as depicted in color as neary true as it is reasonably possible to make the same in a color illustration of this character.

The following is a detailed description of our new variety, with color terminology in accordance with Ridgway's Color Standards and Nomenclature:

Parentage: Seedling.
- *Seed parent.*—An unnamed and unpatented seedling of "New Dawn"×"Geranium Red."
- *Pollen parent.*—"Fashion."

Classification:
- *Botanic.*—Climber.
- *Commercial.*—Climber.

*Flower*

(Observations made from specimens grown outdoors at Newark, New York, during the middle part of the month of August.)

Blooming habit: Recurrent—continuous; everblooming.

Bud:
- *Size.*—Medium.
- *Form.*—Ovoid; is not affected by wet or hot weather.
- *Color.*—When sepals first divide—Rose Red, Plate 12. When petals begin to unfurl—Begonia Rose, Plate 1, very lightly overcast with Rose Red, Plate 12. When half-blown: inside of petals—Rose Red, Plate 12, very lightly overcast with Tyrian Rose, Plate 12; reverse of petals—Rose Red, Plate 12.

- *Sepals.*—Slightly branched; curl back when petals begin to unfurl. Color: inside—Aural Green, Plate 18; outside—Parrot-Green, Plate 6, lightly overcast with Garnet-Brown, Plate 1.
- *Calyx.*—Color—Cedar Green, Plate 6. Shape—funnel. Size—small. Aspect—smooth. Odor when rubbed—none.
- *Peduncle.* — Length — medium. Aspect—rough. Strength—erect; heavy. Color—Garnet Brown, Plate 1.
- *Opening.*—Opens up well; is not affected by adverse weather conditions.

Bloom:
- *Size.*—Large. Average size when fully expanded—4 inches.
- *Borne.*—Both singly and several together; blooms appear on terminal bottom breaks and like "New Dawn" repeat on the side shoots of the older wood.
- *Stems.*—Medium length; normal strength.
- *Form (when first open).*—Open. Permanence—retains its form to the end.
- *Petalage.*—Double (full but open center). Number of petals under normal conditions—from 40 to 45.
- *Color.*—Center of flower—Rose Red, Plate 12. Outer petals—Tyrian Rose, Plate 12, very lightly overcast with Rose Color, Plate 12. Base of petals (aiglet)—Picric Yellow, Plate 4. Inside of petals—Rose Red, Plate 12, lightly overcast with Tyrian Rose, Plate 12. Reverse of petals—Tyrian Rose, Plate 12. General tonality from a distance—Rose Red, Plate 12.
- *Discoloration.*—General tonality at end of first day—Rose Red, Plate 12. Second day—Rose Red, Plate 12, lightly overcast with Tyrian Rose, Plate 12. Third day—Rose Red, Plate 12, lightly overcast with Tyrian Rose, Plate 12.

Petals:
- *Texture.*—Leathery; is not affected by wet or hot weather.
- *Appearance.*—Inside—satiny. Outside—shiny.
- *Form.*—Oval.
- *Arrangement.* — Imbricated (regularly arranged shingle-like).
- *Petaloids in center.*—Few; large.
- *Persistence.*—Drop off cleanly.
- *Fragrance.*—Moderate. Nature — tea (average hybrid tea scent).
- *Lasting quality.*—On plant—long. As cut flower—long.

*Genital organs*

Stamens, anthers: Medium size; many; regularly arranged around styles. Color—Apricot Yellow, Plate 4.
Stamens, filaments (threads): Medium length. Color—Picric Yellow, Plate 4.
Pollen: Color—Maize Yellow, Plate 4.
Styles: Bunched, uneven length; short; thin.
Stigmas: Color—Martius Yellow, Plate 4.
Ovaries: All enclosed in calyx.

*Plant*

Form: Climber.
Growth: Vigorous; branching.
Foliage: Compound of 5–7 leaflets.
- *Size.*—Medium.
- *Quantity.*—Abundant.
- *Color.*—New foliage: upper side—Grass Green, Plate 6, with serrations of Oxblood Red, Plate 1 and center of leaf lightly overcast with Oxblood Red, Plate 1; under side—Madder Brown, Plate 13. Old foliage: upper side—Varley's Green, Plate 18; under side—Courge Green, Plate 17.

*Shape.*—Oval pointed.
*Texture.*—Upper side—leathery. Under side—smooth.
*Ribs and veins.*—Ordinary.
*Edge.*—Serrated (saw-toothed).
*Serration.*—Both double and single; small.
*Leaf stem.*—Color—Cress Green, Plate 31. Under side—prickly.
*Stipules.*—Medium length; smooth.

Wood:
*New wood.*—Color—Rainette Green, Plate 31, lightly overcast with Oxblood Red, Plate 1. Bark—smooth.
*Old wood.*—Color—Cress Green, Plate 31. Bark—smooth.

Thorns:
*Thorns.*—Quantity: on main stalks from base—many; on laterals from stalk—many. Form—flat base; medium length; hooked downward. Color (when young)—Eosine Pink, Plate 1. Position—irregular.

*Prickles.*—Quantity: on main stalks—none; on laterals—none.
*Short needles.*—Quantity: on main stalks—none; on laterals—none.

We claim:

A new and distinct variety of rose plant of the climber class, substantially as herein shown and described, characterized particularly as to novelty by the unique combination of bearing blooms on the terminal bottom breaks, with repeating blooms being borne on the side shoots of the older wood, as in the variety "New Dawn," large double flowers of good petalage, a distinctive and attractive general color tonality of the flowers corresponding to Rose Red, lightly overcast with Tyrian Rose, and a moderate tea flower fragrance.

No references cited.

ABRAHAM G. STONE, *Primary Examiner.*